United States Patent
Thong et al.

[11] Patent Number: 5,843,134
[45] Date of Patent: Dec. 1, 1998

[54] THERAPY DEVICE

[75] Inventors: Tran Thong; Dennis Digby, both of Lake Oswego, Oreg.; Max Schaldach, Erlangen, Germany

[73] Assignee: Biotronik Mess- und Therapiegeraete GmbH & Co. Ingenieurbuero Berlin, Berlin, Germany

[21] Appl. No.: 810,014

[22] Filed: Mar. 3, 1997

[30] Foreign Application Priority Data

Mar. 4, 1996 [DE] Germany .................. 196 09 362.7

[51] Int. Cl.$^6$ .................................. A61N 1/365
[52] U.S. Cl. .............................................. 607/17
[58] Field of Search ........................ 607/17, 9, 18

[56] References Cited

U.S. PATENT DOCUMENTS 4,181,133  1/1980  Kolenik et al. .
4,300,567  11/1981  Kolenik et al. .
5,379,776  1/1995  Murphy et al. .

FOREIGN PATENT DOCUMENTS

94/10922  5/1994  WIPO .

*Primary Examiner*—Scott M. Getzow
*Attorney, Agent, or Firm*—Spencer & Frank

[57] ABSTRACT

A therapy device having at least one sensor for detecting a variable that can be measured on the body of a patient in the application of a predetermined therapy, and for outputting a corresponding measured value, an evaluating and control device that is connected to the output of the sensor, and a therapy device that is connected to the output of the evaluating and control device and is configured for realizing different therapies as a function of the association of the value of the measured variable with a predetermined value range, with the evaluating and control device having a range-limit memory, a comparator unit for associating the measured value of the variable with one of the value ranges, a therapy memory having at least two separately-addressable memory regions for storing at least two different values of the therapy-control variable in association with the values of the measured variable within an overlap zone between two value ranges, a past-history memory and past-history evaluation means for transmitting the address data expressing the evaluation result to the therapy memory for reading out exactly one value of the therapy-control variable.

18 Claims, 5 Drawing Sheets

THERAPY DEVICE

FIELD OF THE INVENTION

The invention relates to a therapy device of the type disclosed in the preamble to claim 1.

DESCRIPTION OF THE BACKGROUND ART

Automatic medical therapy devices are generally known, and have been used for a long time, particularly in everyday medical applications, as implantable cardiac pacemakers for treating bradycardic and/or tachycardiac disordered heart action, but also increasingly as automatic defibrillators or cardioverters, as combined pacemaker/cardioverters, or as implanted medication-dosing pumps or the like.

Also known are generic devices that are equipped with one or a plurality of sensors for receiving diagnostically-relevant signals in the patient's body, and associated signal-conditioning and -processing devices, as well as an evaluating and control unit. In accordance with an algorithm stored in the device, this unit calculates a current parameter or set of parameters from the plurality of programmed operating parameters or therapy variables as a function of the value or values of the received variable(s). Examples of these devices include pacemakers in which the stimulation rate is controlled as a function of the physical activity of the carrier. Other therapy devices are known that are configured for automatic activation, or—particularly also pre-programmed—switching from one mode of operation to another as a function of the value of a variable detected in the patient's body. Among these are the known demand pacemakers or automatic defibrillators, and the recently-developed combination devices.

Since the development and clinical application of so-called demand pacemakers, it has been known to control pacemakers particularly such that the spontaneous cardiac actions are detected, and the value of the heart rate or the time intervals between specific cardiac actions (e.g. the RR intervals between consecutive ventricular actions) are determined and compared to a predetermined nominal value, and the pacemaker emits stimulation pulses precisely when the measured value does not lie within a range limited by the nominal value.

Modern devices of this type are microprocessor-controlled, and offer the option of individually programming one of a plurality of pre-installed operating modes and associated operating parameters (referred to hereinafter as therapy variables insofar as they are relevant to the therapy) tailored to a concrete illness profile; this programming effects a predetermined therapy.

Within the scope of these devices, the concept of the demand pacemaker has been developed significantly to yield the universal demand cardiac-rhythm correction device. Some of these developments are based on a continually more precise subdivision of the heart-rate or RR-interval continuum, and, as a function of the range in which of the plurality of predetermined ranges a current measured value lies, one of a plurality of defined, respectively unambiguous therapies associated with a range is implemented. With a device of this type, a classic demand-pacemaker operation can be realized in the case of bradycardia, just as conventional therapies can be realized for different tachycardias (refer to U.S. Pat. No. 4,181,133) or, possibly, a defibrillation shock therapy (U.S. Pat. No. 4,300,567).

Based on the recognition that the association of the heart rate with one of the predetermined ranges by itself does not always reliably permit the determination of the appropriate therapy, the efforts of recent years included an emphasis on testing additional classification criteria and taking them into consideration in the control algorithms—refer to U.S. Pat. No. 5,379,776 (including sources cited therein).

Devices of the known type are programmed during implantation corresponding to the illness profile, and possibly the living conditions (for example the average physical activity) of the patient, with the algorithm for determining the therapy or therapy value(s) also being established as a function of the value(s) detected in the body. In the post-operative examinations, which are performed at specific intervals, the operating mode and set of operating parameters and, if need be—in the case that the therapy device utilizes a plurality of stored algorithms—the control algorithm to be used can be changed through reprogramming.

However, in the operating phases between the examinations, the activated algorithm unequivocally reveals which therapy or therapy variable the device provides in a specific value range of the measured variable detected in (or on) the body—for example, at which limit heart rates a predetermined stimulation is used to treat a bradycardia or tachycardia or a switch is made from one stimulation mode to another. This association, which is made at a specific time and is based on a specific physical state of the patient, must, however, in no way be strictly in effect. In particular, a previous therapy or a (superficially unsuccessful) therapy experiment may have already latently changed the patient's physical state.

With a more complex classification method and/or the essentially simultaneous detection and evaluation of the signals of a plurality of sensors, the patient's current physical state can be ascertained with increasing precision; this, however, does not change the disadvantageous, strong determinate nature of the therapy because of the measured variable(s).

It is the object of the invention to modify a therapy device of the type mentioned at the outset such that, because of a predetermined evaluating and control algorithm, the device is capable of providing a therapy that is, on the one hand, as gentle as possible, but on the other hand, as fast-acting as possible, taking into consideration the past history of the therapy, without becoming significantly more complex and costly.

SUMMARY OF THE INVENTION

This object is accomplished by a therapy device having the features of claim 1.

The invention includes the concept of creating a device having means that make relative the strong determinate nature of the therapy or therapy variable due to the position of a measured variable in a range having clearly-defined limits, this nature being inherent to previous solutions, in that overlap zones are defined between the ranges in which different therapies or therapy variables are realized as a function of the past history of the therapy. In connection with an ambiguous association of therapies or therapy variables, such a range overlap particularly requires additional memory means and further-developed processing means; in view of the low specific costs, however, the additional expense is non-problematic.

A useful embodiment of the process control includes a timer and a measured-value comparator unit that is clocked by the timer, and is connected by way of a first input to the sensor for the current values of the measured variable to be detected in the body, and by way of a second input to the range-limit memory. With control by the timer, the current value of the measured variable is periodically queried and compared to the stored limits, and an access-control and address signal that characterizes the result of the comparison is outputted; this signal effects a read-out, from the first therapy memory, of the value of the therapy-control variable with which a therapy or therapy variable associated with the relevant measuring range is controlled—or prevents the read-out entirely. In the latter case, the last valid value of the therapy-control variable, that is, the ongoing therapy, is maintained. The process control can also be configured such that an access-control signal is outputted for a read-out from the first therapy memory only after it has been determined that a value-range limit has been exceeded.

To embody the described arrangement, the process control includes a measured-value memory for at least the respectively last-queried measured value, and the measured-value comparator unit is also connected to this memory and thus configured such that the outputted access-control and address signal characterizes an exceeding of a range limit with respect to the last detection of a measured value. The measured-value memory can—at a somewhat higher cost— also be configured as a trend memory for a temporal sequence of previous measured values, in which case means for performing a trend calculation for the measured values are provided instead of the comparator unit.

In a special configuration as an implantable demand pacemaker, the therapy device is equipped with a range-limit memory provided for storing at least one limit between a normal and a bradycardic rate range, and two limits and thus an overlap zone between the normal and a tachycardiac rate range; the device is further equipped with a first therapy memory configured for storing at least one bradycardia and tachycardia therapy (known per se), respectively.

In a further special configuration as an implantable anti-tachycardia pacemaker/defibrillator, the range-limit memory is configured to store at least one limit between a normal and a tachycardia rate range, and two limits and thus an overlap zone between the tachycardia rate range and a fibrillation range. Moreover, in a combination device of this type, the range-limit memory can respectively include two memory regions for storing two limits between the normal and the tachycardia rate range, and the tachycardia rate range and the fibrillation range, respectively, with the therapy association in the two overlap zones naturally being correspondingly ambiguous. This also applies for a more-refined configuration for differentiated treatment of qualitatively-different tachycardia types, in which the range-limit memory has memory regions for two tachycardia rate ranges that are adjacent over an overlap zone between two limits.

Known demand pacemaker-hysteresis functions can advantageously be performed simultaneously with a pacemaker or combination device in which the range-limit memory has two memory regions for storing two limits and thus an overlap zone between the normal and the bradycardia rate range.

An embodiment variation of the invention in which devices that react particularly sensitively and flexibly to changes in the therapy requirement includes the concept of creating a device having means that make the strong determinate nature of the therapy or therapy variable due to the measured variable(s) relative by impressing the latter with an arbitrary, temporal fluctuation during the course of the evaluation. This results in a pseudo-measured variable that is corrected with the fluctuation value and whose further evaluation with the established algorithm leads to the output of a varied therapy (therapy variable). This variation of the therapy permits a comparative success check, on the basis of which the therapy can be optimized (without a change in the algorithm).

The success check can particularly be effected by means of an additional sensor that ascertains the physical state of the patient as precisely as possible insofar as the therapy device is used for influencing this state. As an alternative, the check can be performed by way of the sensor that is also used to obtain the primary measured variable—with the aid of measured values and evaluation criteria stored in association with each other in advance. The more or most successful varied therapy or therapies is or are then determined as being currently valid. Depending on the concrete task and configuration of the therapy device, different strategies can be followed, and corresponding technical means can be used, which will be discussed in detail below.

For some embodiments, special means for a comparative success check can even be omitted, provided that the effect of a one-time-varied therapy causes an automatic halt to any therapy (at least temporarily)—for example, an effective pulse sequence emitted because of the measured value of the heart rate, which is affected by fluctuations, in order to end an accelerating tachycardia, or, analogously, a cardioversion pulse at the onset of fibrillations—or because, based on fundamental considerations, an advanced, slight fluctuation in the therapy variable due to the fluctuation impressed upon the measured variable can be regarded as advantageous, for example for a medication-dosing device under certain circumstances.

In a practical embodiment that includes a single sensor, a comparison-value memory is associated with the sensor, and a comparator unit connected on the input side to the outputs of the sensor and the comparison-value memory are provided for control and for simultaneously performing a success check. In the comparator unit, the measured value of the sensor is subjected to a comparison with at least one stored comparison value, and the unit outputs a control signal as the result of the comparison; on the basis of this signal, the measured value of the sensor is supplied to either the input of the mathematical processing unit—for processing with a fluctuation value—or, bypassing this unit, directly to the input of the evaluating and control device.

In contrast, in a dual-sensor device, a first and a second sensor are provided, with the fluctuation-value generator being associated with the output of the first sensor such that measured values of the first sensor that have been corrected with the fluctuation value form the basis of the variation of the therapy or therapy variable, while the output of the second sensor is at least indirectly connected to an input of the time-control unit such that the impression of the fluctuation variable onto the measured values of the first sensor is controlled, selectively prevented in particular, as a function of the measured values of the second sensor.

To detect an activity variable or a variable that characterizes an organ function of the patient, and/or to detect the therapy variable, the above-described sensor or first sensor can be configured as, for example, an intracardiac electrode having a downstream sensing amplifier for electrical cardiac activity, particularly with an associated device for determining the period of electrical cardiac activity as a measured value. The second sensor is preferably configured to detect a variable that is dependent on an organ function or the therapy variable, specifically one that is characteristic of the overall physical or hemodynamic state of the patient; for example, the sensor can be a blood-pressure sensor.

Depending on the concrete application, the fluctuation-value processing of the measured variable can advisably be effected through addition/subtraction or multiplication/division. Correspondingly, the fluctuation-value generator is configured to output at least one increment or decrement value and the mathematical processing unit is configured as an addition stage, or the fluctuation-value generator is configured to output at least one correction factor and the mathematical processing unit is configured as a multiplication stage. In particular, the fluctuation-value generator includes a fluctuation-value memory for a plurality of fluctuation values and, optionally, a random-number generator for respectively selecting one of the stored fluctuation values for impression onto the measured value.

In the configuration of the therapy device as a cardioverter, particularly an implantable one, the sensor or the first sensor can advisably be formed by an intracardiac electrode having a downstream sensing amplifier, and can include a device for determining the period of electrical cardiac activity as a measured value. The evaluating and control device in this instance is configured to establish at least one predetermined sequence of electrical stimulation pulses and/or a high-energy individual pulse, and the therapy device can be configured to generate and emit the corresponding electrical stimulation pulses.

A completely different embodiment involves the configuration of the device as a particularly implantable medication-dosing device in which the sensor or the first sensor is configured to detect the level of an agent, or a variable dependent thereon, in the patient's body, and the configuration of the evaluating and control device to establish a medication dose per time unit, and the configuration of the therapy device to administer the dose established per time unit to the body. In a special configuration for medicinal treatment of cardiac arrhythmia, the measured value can also be particularly detected here by way of an intracardiac electrode, because the cardiac actions naturally reflect the arrhythmia to be treated, as well as the success of the treatment.

BRIEF DESCRIPTION OF THE DRAWINGS

Advantageous modifications of the invention are characterized in the dependent claims or described in detail below in the description of preferred embodiment of the invention, in conjunction with the figures. Shown are in:

DESCRIPTION OF THE PREFERRED EMBODIMENTS

Figure 1:
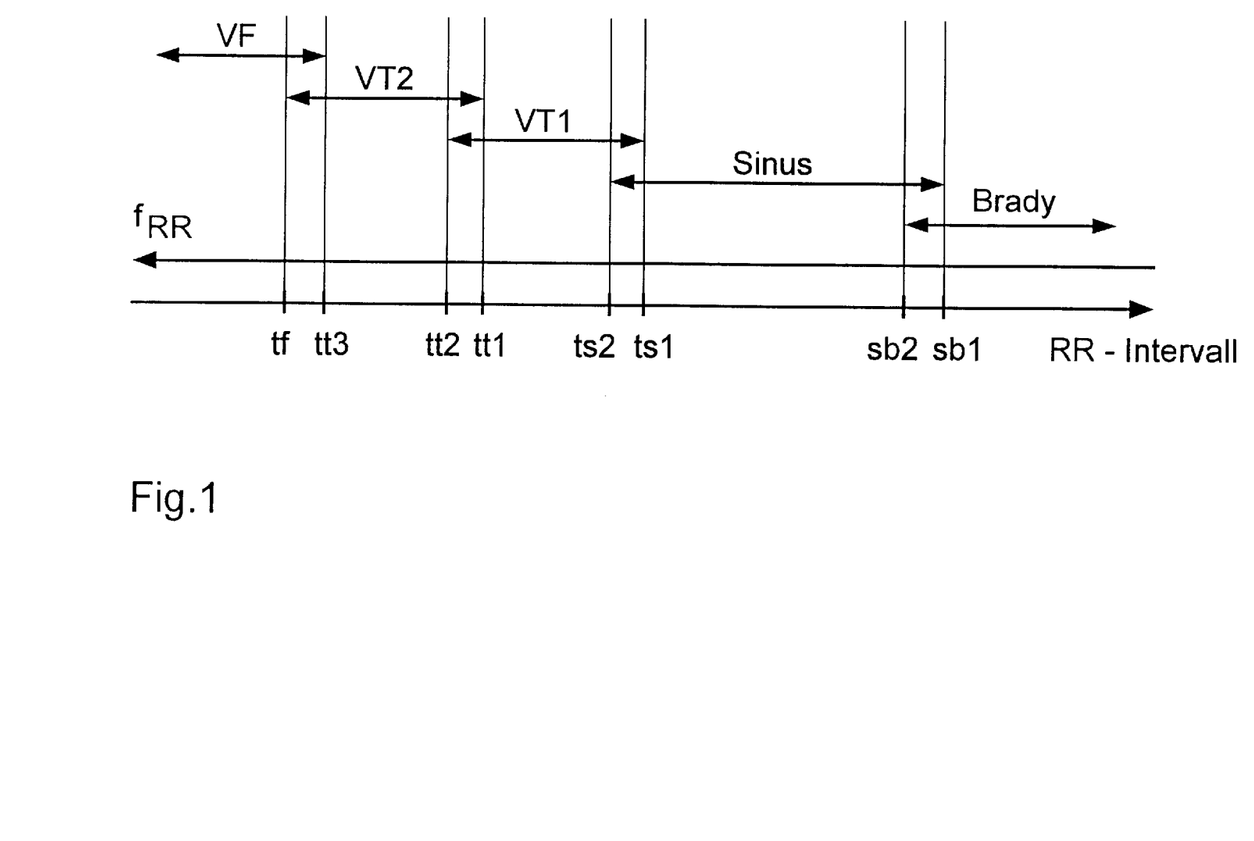
FIG. 1 a schematic representation of the heart-rate continuum, divided into different sections, for illustrating the function of a combined pacemaker/defibrillator according to a preferred embodiment of the invention, FIG. 2 a greatly-simplified block diagram of a combined pacemaker/defibrillator according to an embodiment of the invention related to FIG. 1, FIG. 3 a schematic representation of the operation of the combined pacemaker/defibrillator according to FIG. 2, FIG. 4 a greatly-simplified function block diagram of a medication-dosing device for anti-arrhythmia medication in accordance with a further embodiment of the invention, and FIG. 4a a simplified block diagram of an embodiment of the evaluating and control unit of the device according to FIG. 4.

FIG. 1 is a schematic representation of the heart-rate continuum, divided into different, overlapping sections for illustrating the function of such a device. The RR interval (with values increasing to the right) or the heart rate $f_{RR}$ (with values increasing to the left) is shown on the x axis. "VF" represents the range of ventricular fibrillation, with "VT2" and "VT1" being two adjacent ranges of ventricular tachycardia having different diagnostic and therapeutic relevance, "Sinus" represents the range of normal cardiac activity, and "Brady" represents the range of an unacceptably-low heart rate, that is, a (ventricular) bradycardia. The measurement of a value of fRR outside of the "Sinus" range essentially requires a specific stimulation of the heart for returning to the normal range, with the type of stimulation and its physiological effects on the patient differing substantially.

The limits (respectively doubled due to the mentioned overlap) between the individual ranges are represented by "tf," "tt3," "tt2," "tt1," "ts2," "ts1," "sb2" and "sb1"; the significance of the overlap ranges is disclosed below.

Figure 2:
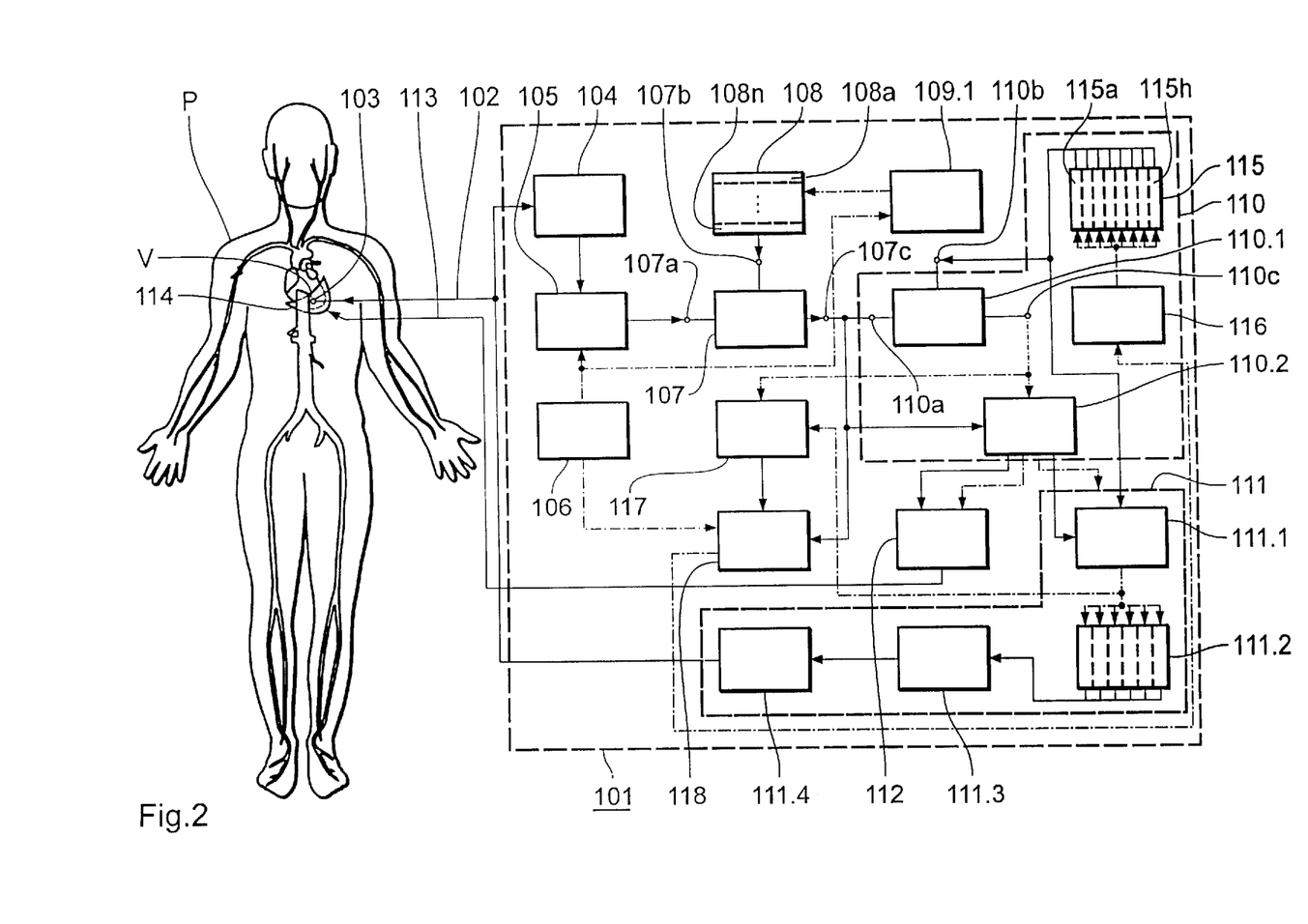

FIG. 2 is a greatly-simplified block diagram of a combined pacemaker/defibrillator 101 according to an embodiment related to FIG. 1, the device being connected in a manner known per se by way of an electrode line 102 to a cardiac electrode 103 fixed in the ventricle.

The proximal end of the electrode line 102 is connected to an input-amplifier stage 104 that (in a pacemaker design per se) has filter and amplifier stages for signal conditioning, and at whose output a level-adapted cardiac signal that is extensively free from interference is present. The output of the input stage 104 is connected to the signal input of a counter stage 105, whose clock input is connected to a clock generator or timer 106, and in which the rate $f_{RR}$ of the detected cardiac actions (ventricle depolarizations or R waves) is determined.

The output of the counter stage 105 is connected by way of a measured-signal input 107a to an addition stage 107, and an increment/decrement memory 108 is provided for cardiacrate correction values to be taken into consideration through addition or substraction (i.e., positive or negative). With time control or clocking by the timer 106, a plurality of correction values for the current value of the heart rate $f_{RR}$ stored according to the randomness principle is sequentially read out of the memory 108, and read into the addition stage 107 by way of its second input 107b, and used there to correct the current measured value supplied by way of the first input 107a. The sum or difference (or, in the interim, the uncorrected measured value) is outputted at the output 107c.

It is assumed here that the memory 108 utilizes a plurality of memory regions 108a through 108n, in which increment/decrement values in a scatter range of, for example, ±25 ms are stored, and that their addressing is effected in a statistical manner by way of a random-number generator 109.1. The scatter range of the increment/decrement values can also be defined or programmed as patient-specific, for example, as a fraction of the measured RR interval; it is critical, however, that the control of the therapy be effected essentially with reference to a measured value detected definitively in or on the body. In particular, if the addressable increment and decrement values are distributed uniformly in the scatter range, the use of a random-number generator ensures that the temporal average value of the correction quantity is zero.

The output 107c of the addition stage 107 is connected by way of a signal input 110a of a therapy pre-selection unit 110 to a control input of a pacemaker stage 111, on the one hand, and on the other hand to a control input of a cardioverter stage 112, so the RR-interval measured value or summation value present at the output of the stage 107 can serve in actuating a pacemaker for outputting anti-bradycardic or anti-tachycardiac pulse sequences, or in triggering a high-energy shock pulse (defibrillation or cardioversion pulse).

The output of the pacemaker stage 111 is connected by way of the electrode line 102 to the ventricle electrode 103, which therefore performs a dual function as a sensor electrode of the combination device 101 and a stimulation electrode of its pacemaker stage 111. The output of the cardioverter stage 112 is connected by way of a second, intrathoracically-laid electrode line 113 to a defibrillation surface electrode 114 disposed epicardially on the heart H, by way of which, as needed, the high energy of a defibrillator shock is transmitted to the excitable heart tissue with an energy density that is still tolerable to the tissue.

The therapy pre-selection unit 110 encompasses a comparator 110.1, which is connected by way of a first data input to the addition stage 107, and by way of a second data input 110b to two separately-addressable memory regions 115a, 115b of a range-limit memory 115. In these regions, the two limits tf and tt3 of the ranges VF and VT2, which were mentioned above with reference to FIG. 1, are stored in the RR-interval or heart-rate continuum as patient-specific, pre-programmed values. Associated with the range-limit memory 115 is an address selector or memory 116, which—as will be described in more detail below—connects one of the two memory regions 115a, 115b to the comparator 110.1, but blocks the other one, as a function of an internal control signal that reflects the past history of the therapy. The comparator 110.1 is connected on the output side to a changeover switch 110.2, which activates the pacemaker stage 111 or the cardioverter stage 112 depending on the result of the comparison of the current output value of the addition stage 107 with the stored range-limit value tf or tt3, and, possibly, simultaneously switches the above-mentioned output value through to the pacemaker stage 111.

The pacemaker stage 111 has a multiple-stage comparator unit 111.1, which—similarly to the therapy pre-selection unit 110—is connected by way of two inputs to memory regions 115c through 116h of the range-limit memory 115, with respectively one of the regions 115c (value tt2) or 115d (value tt1), 115e (value ts2) or 115f (value ts1), or 115g (value sb2) or 115h (value sb1) being addressed or blocked by way of the address selector 116 as a function of the past history of the therapy. In the multiple-stage comparator unit 111.1 the output value of the addition stage 107 is sequentially compared to the different range limits and, as a function of the result of the comparison, a signal that expresses the association of the output signal of the stage 107 with one of the above-mentioned heart-rate ranges or RR-interval ranges is outputted at the output of the comparator unit 111.1.

This signal is supplied to a pulse-sequence control-signal memory 111.2 for addressing, whereupon a pre-stored pulse sequence pattern (which is distinguished particularly by a predetermined stimulation rate, but possibly also by a specific design and further parameters) is transmitted from the respectively addressed memory location to a pacemaker-pulse generator 111.3. This generator generates a sequence of pulses that corresponds to the pulse-sequence pattern; the pulses pass through an output stage 111.4 in a conventional manner, and are transmitted to the heart H by way of the electrode 103 in the event that the pacemaker stage 111 is activated. According to the above description, this is the case when the output signal of the stage 307 [sic] is to be associated with one of the ranges VT2, VT1 or Brady.

If, in contrast, in the case of an output signal of the stage 107 within the rate range VF, the cardioverter stage 112 is activated, a single shock pulse having pre-programmed parameters is generated there (in a manner known per se) and transmitted to the heart H by way of the electrode 114.

Both the output of the comparator 110.1 in the therapy pre-selection unit 110 and the output of the multiple-stage comparator unit 111.1 are additionally connected to a measured-value memory 117, which is addressed with each change—detected in the comparator stages 110.1 or 111.1—in the association of the output value of the addition stage 107 for one of the above-mentioned ranges of the heart-rate or RR-interval continuum for storing the respectively current association, and in which a predetermined number of associations (that reflect the past history of the therapy in a certain sense) of the heart rate or the RR interval from the past is stored. In the simplest case, only the association prior to the respectively last change is stored; in a more costly embodiment organized in accordance with the LIFO (Last In, First Out) principle and having a plurality of memory regions, the memory 117 operates as a regular trend memory.

The measured-value memory 117 is connected to an input of a trend-evaluation stage 118, which is additionally connected by way of a further input to the output of the addition stage 107, whose input is connected to the address selector 116. By way of at least one change stage, the trend-evaluation stage 118 delivers the above-mentioned control signal for the address selector or pointer 116 as the result of the evaluation of the development over time of the heart-rate or RR-interval association—starting from the current value. By way of the selector, the current range association of the output signal of the stage 107 valid in the overlap regions tf–tt3, tt2–tt1, ts2–ts1 and sb2–sb1, and therefore the valid therapy (defibrillation shock or anti-tachycardiac pulse sequence or demand-stimulation pulse sequence to be applied affirmatively) is again determined (in accordance with the above description).

The cooperation of the above-described function units according to FIG. 2, particularly with respect to the therapy control in the overlap regions, is discussed below using as examples special situations that can occur in a patient disposed to certain tachycardiac disordered heart action, in which the heart rate or RR interval can fall into the ranges VT1, VT2 or VF:

In principle, a specific electrostimulation therapy (i.e., a set of stimulation parameters) is associated with each of the ranges over the RR axis in FIG. 1. It should be kept in mind that "RR rate" or "RR interval" is to be understood as a measured value that has been corrected with a fluctuation increment or decrement. If the measured value (the output signal of the addition stage 107) affected by the fluctuation variable changes within a range, no change is made to the therapy. If, however, it exceeds a range limit, the pacemaker/cardioverter shown schematically in FIG. 2 basically switches to another of a plurality of predetermined therapies. As a consequence of the influence of the statistical fluctuation variable, in measured values that lie within the range regions near the limits, occasionally a switch is made between different therapies; in other words, the fluctuation variable permits a "test" of different therapies or therapy variables.

If, in the present embodiment, as the result of an acceleration of a tachycardia, the heart rate (affected by fluctuation) goes from the VT1 range into the overlap region with the VT2 range between the limit values tt1 and tt2, a switch is made to the therapy that is valid for the range VT2 ("more aggressive"). This is therapeutically logical, because the therapy applied in the VT1 range ("less aggressive")

proved too weak to prevent the acceleration of the tachycardia. If the heart rate likewise enters the overlap region tt1–tt2 over the course of the retardation of a tachycardia that was originally in the VT2 range, the therapy that is valid for the VT2 range is maintained, which is also logical, because this therapy has proven successful.

If, in contrast, the heart rate jumps from the Sinus range into the same overlap region tt2–tt1 of the VT1, VT2 ranges, the therapy (pulse sequence) for the VT1 range, not for the VT2 range, is initiated. This procedure is based on the consideration that, in this development, the patient's body is not intended to be stressed without transition by the "more aggressive" therapy for the VT2 range as long as the therapy valid for the VT1 range has not been applied experimentally. This should also minimize the risk of inducing a further acceleration of the tachycardia through the therapy itself. The therapy valid for the VT2 range is not applied until the heart rate increases further such that it leaves the overlap region.

The valid therapy is also selected, correspondingly differentiated, in an either slow or drastic transition of the heart rate into the overlap region tf–tt3 between the VT2 and VF ranges. The overlap regions ts1–ts2 between the Sinus and VT1 ranges, and sb1–sb2 between the Brady and Sinus ranges can, however, be treated as "classic" hysteresis regions, in which the selection of therapy is only a function of the direction of the entrance into the overlap region.

Figure 3:
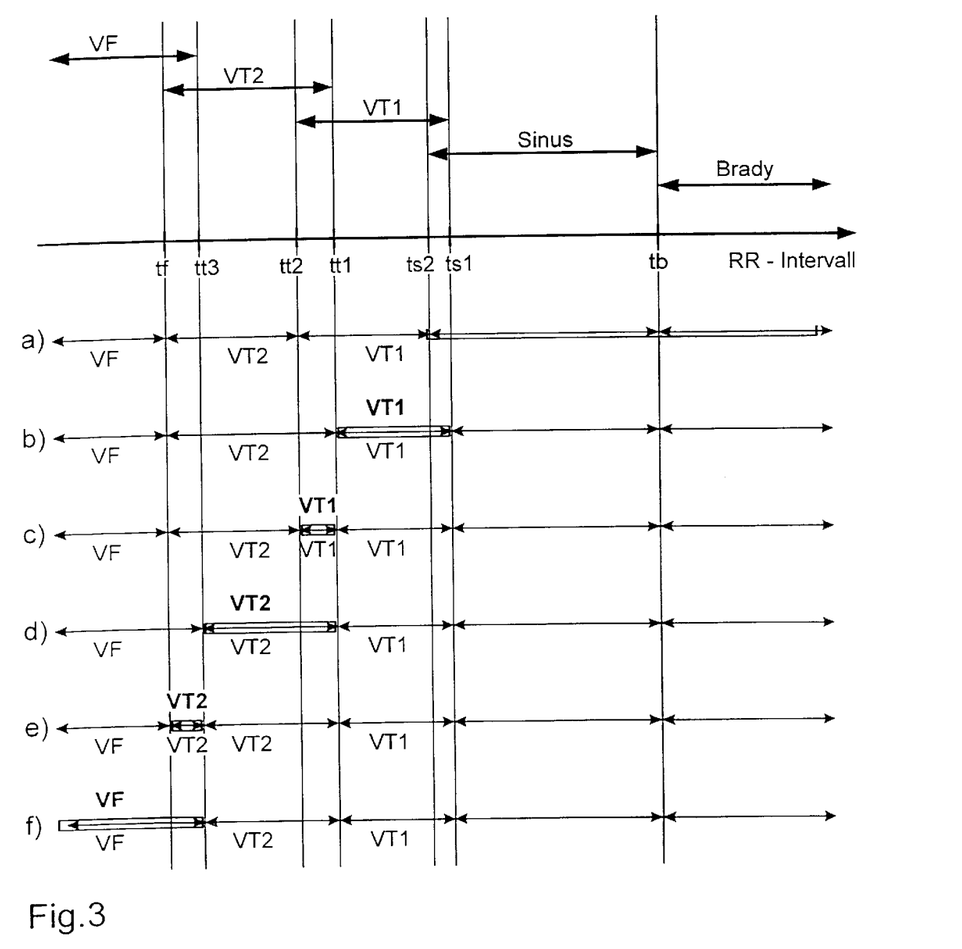

The outlined function of the pacemaker/cardioverter according to the present embodiment is illustrated in FIG. 3, with the range subdivision essentially corresponding to that of FIG. 1 (only the overlap region sb1–sb2 between the Brady and Sinus ranges is omitted here):

Line a) shows that, if the heart rate lies in one of the ranges of Brady or Sinus in a first phase, and no therapy or bradycardia stimulation is used, in a subsequent acceleration into the rate range between ts2 and tt1, the therapy "VT1" is applied between ts2 and tt1, the therapy "VT2" is applied between tt2 and tf, and the therapy "VF" is applied above tf.

Line b) shows that, if the rate was initially in the region between ts1 and tt1, and VT1 was the therapy applied (which, incidentally, only applies for RR values between ts1 and ts2 as described above, if this range was reached over the course of the retardation of a tachycardia), a subsequent transition into the region between tt1 and tf leads to the application of the therapy "VT2," but a transition to a value above tf leads to the application of the therapy "VF." A retardation into the region between tb and ts1 leads to discontinuation of any therapy, and, lower than tb, to a bradycardic stimulation—which also applies for the following lines.

Line c) shows that, if the rate was initially in the region between tt1 and tt2, and the therapy "VT1" was correspondingly applied (which, according to the above discussion, is only the case if the region was attained over the course of a rapidly-accelerating tachycardia), a subsequent transition into the region between tt2 and tf leads to the application of the therapy "VT2," a transition to a value above tf leads to the application of the therapy "VF," but with a retardation of the tachycardia into the region between ts1 and tt1, the therapy "VT1" is maintained.

Line d) shows that, if the rate was initially in the region between tt1 and tt3 and the therapy "VT2" was applied, a subsequent transition to a value above tt3 leads to the application of the therapy "VF." A retardation into the region between ts1 and tt1 leads to a switch to the therapy "VT1." The latter also applies for lines e) and f).

Line e) shows that, if the rate was initially in the region between tt3 and tf and, correspondingly, the therapy "VT2" was applied, a subsequent transition to a value above tf leads to the application of the therapy "VF," but with a retardation into the region between tt1 and tt3, the therapy "VT2" is maintained.

Finally, line f) shows that, starting at a rate above tt3, at which the therapy VF was applied, a retardation into the region between tt1 and tt3 leads to a switch to the therapy "VT2."

Figure 4:
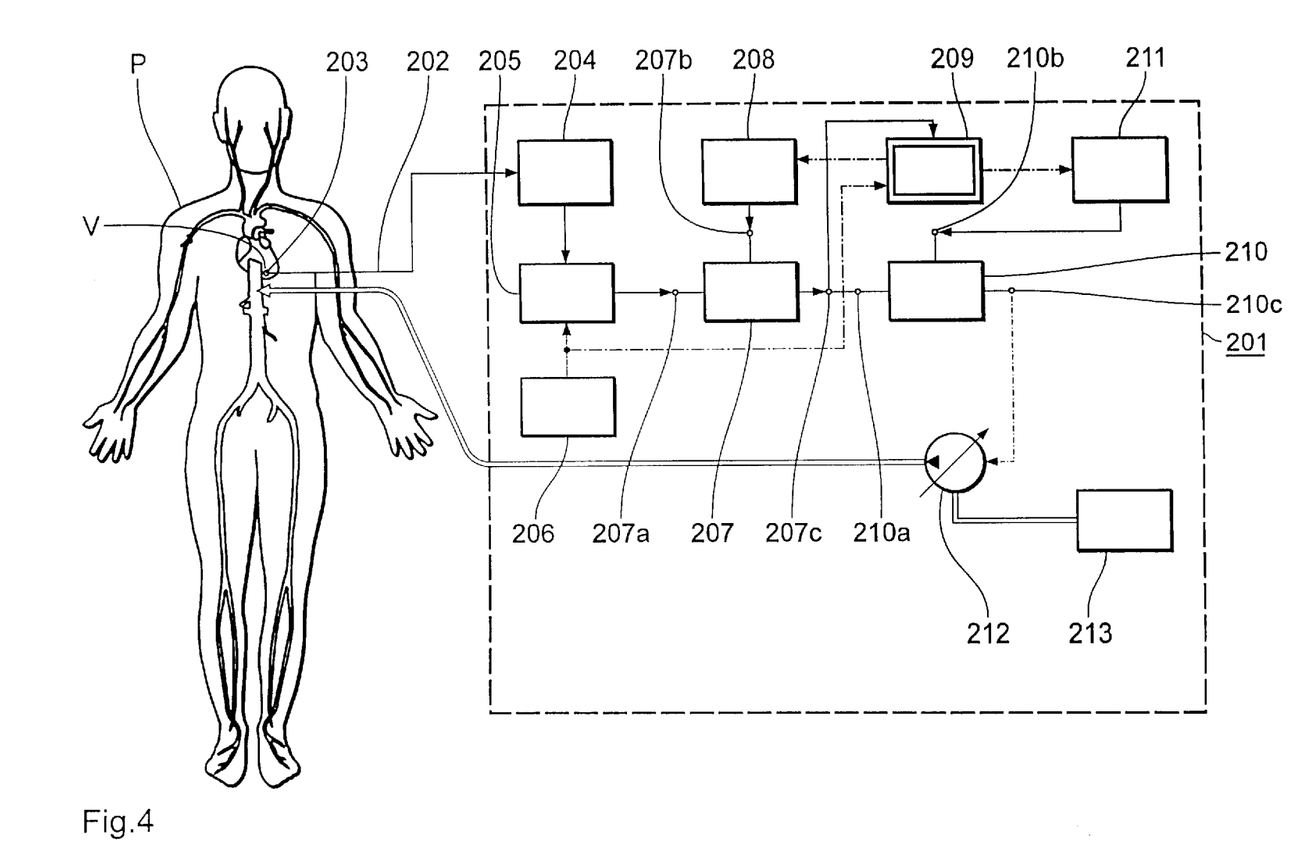

Like FIG. 2, FIG. 4 is a greatly-simplified function block diagram of a medication-dosing device 201, particularly for medications for correcting cardiac arrhythmia. The embodiment described below is basically suited for controlling an automatic medicinal treatment of sudden, life-threatening bradycardia or tachycardia using suitable anti-arrhythmia medication.

The device 201 is connected by way of an electrode line 202 to an intracardiac electrode 203 positioned in the ventricle V of a heart H for receiving cardiac-action potentials. The proximal end of the electrode line 202 is connected to an input-amplifier stage 204 that (in a pacemaker design per se) has filter and amplifier stages for signal conditioning, and at whose output a level-adapted cardiac signal that is extensively free from interference is present. The output of the input stage 204 is connected to the signal input of a counter stage 205, whose clock input is connected to a clock generator or timer 206, and in which the rate $f_{RR}$ of the detected cardiac actions (ventricle depolarizations or R waves) is determined.

Similarly to the arrangement of FIG. 2, the output of the counter stage 205 is connected by way of a measured-signal input 207a to an addition stage 207, and an increment/decrement memory 208 is provided for cardiac-rate correction values to be taken into consideration through addition or substraction (i.e., positive or negative). With control by a program-control unit 209, which is connected to the clock generator 206 and is described in more detail below, a fluctuation-value processing of the measured heart rate is performed; the processing essentially corresponds to the arrangement of FIG. 2 (and is therefore not explained again here).

The output 207c is connected to a first signal input 210a of an evaluating and pump-actuating unit 210, which is connected by way of a second signal input 210b to a dosage-data memory 211. The design and organization of this memory essentially correspond to those of the memory 111.2 of FIG. 2; in the present embodiment, an association table for heart rate-medication dose is stored in the memory. The respective dosage value read out of the addressed memory location is the basis of the determination of an associated control variable that is internal to the device and is made available at the output 210c of the evaluating and pump-actuating unit 210. This output is connected to a dosing pump 212, by way of which the calculated dosage of an anti-arrhythmia medication stored in a medication tank 213 can be administered into the body of the patient P. With a dangerous drop or rise in the heart rate into a critical range (depending on the use of the device for therapy for bradycardic or tachycardiac disordered heart actions), a medicinal treatment is therefore initiated automatically, the success of which can be checked using the signals received by way of the cardiac electrode 203.

The current heart rate corresponding to the effect of the injected medication and detected by way of the electrode 203, the input stage 204 and the counter stage 205 is again subjected to the above-described processing. In the present embodiment, it must be kept in mind that the dosing device 201 is intended to effect emergency therapy, that is, the dosing pump 212 should not operate in normal situations. Correspondingly, the pre-stored increment or decrement values and the association table for heart rate and medication dosage are also to be selected to match one another such that medication is only administered with measured values that are also affected by correction, which are to be allocated to a range that is fairly likely to be critical for the patient.

Detection and storage of a therapeutically-advantageous increment or decrement value can be omitted here, because in emergency therapy it is less critical whether the original, or one (and which) of the varied heart rate measured values, was the starting point for an effective medicinal treatment; a far more decisive factor is that the treatment was efficient. In addition, the patient-stipulated conditions can change considerably, up to a possible recurrence of bradycardia or tachycardia, so the variation of the therapy control should then be effected, possibly advisably, from the same "neutral" starting point—namely the current measured value.

Figure 4A:
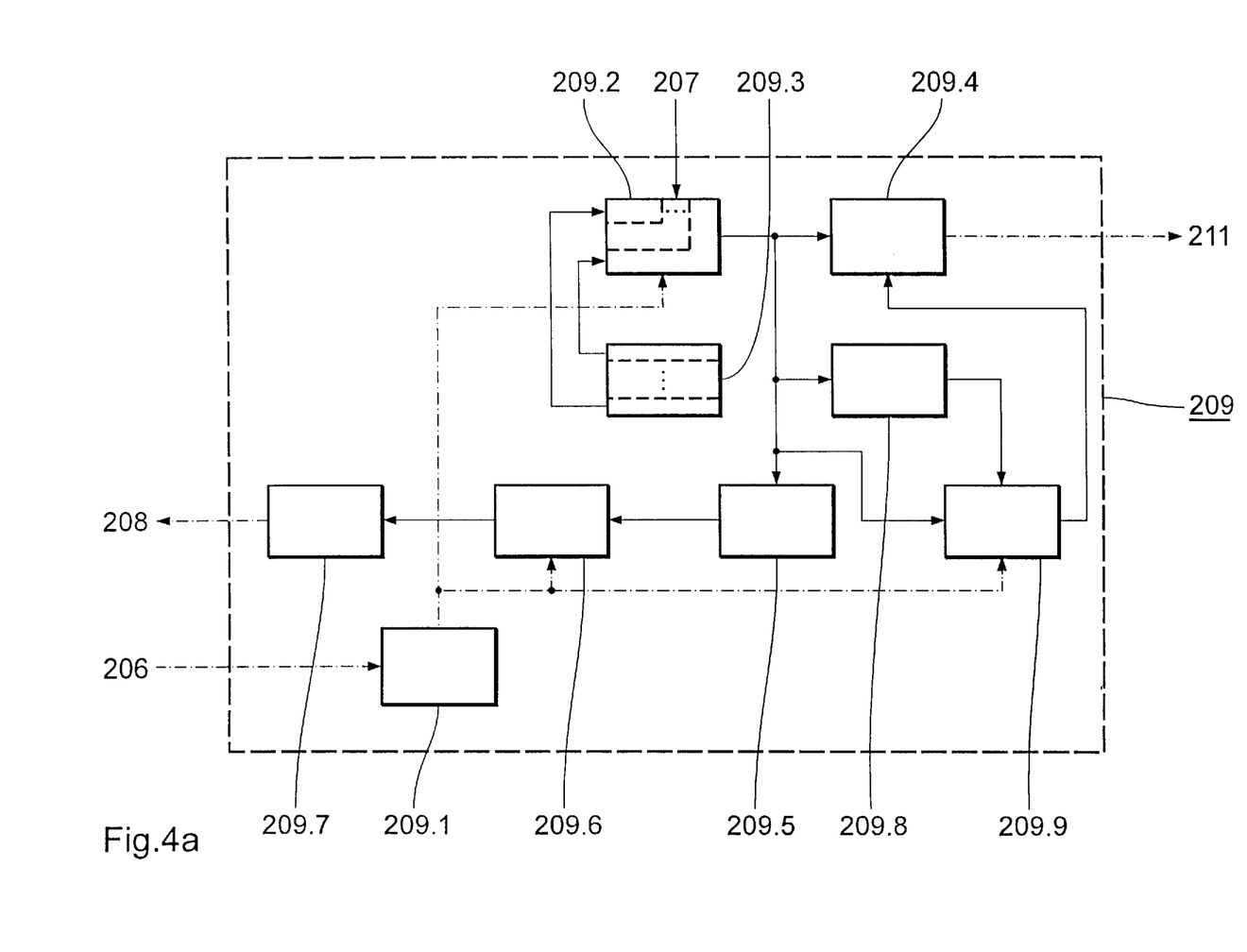

FIG. 4a shows a simplified function block diagram of an embodiment of the evaluating and control unit 209 of the medication-dosing device 201 according to FIG. 4. It should be kept in mind that this unit—like the function groups for controlling the device shown in FIG. 2—is essentially configured in practice as a microcontroller having a close link between hardware- and software-related implementation.

The evaluation and control unit includes an internal process control 209.1, which is clocked by the timer 206 and periodically activates a multiple-stage comparator unit 209.2, which is connected by way of an input to the output of the addition stage 207 and can be connected sequentially, by way of a further input, to the memory regions of a measuring-range memory 209.3 configured as an EPROM. The comparator unit 209.2 is connected on the output side to an address pointer 209.4, in which the output signal of the comparator unit is converted into an address signal for the dosage-value memory 211. The comparator unit is further connected to a digital filter 209.5, which only permits predetermined output signals of the comparator unit to reach an input of an AND gate 209.6, at whose other input the clock signal of the process control 209.1 is present. The output of the AND gate 209.6 is connected to a random-number generator 209.7, at whose output an address signal for the increment/decrement memory 208 is available.

The output of the comparator unit 209.2 is further connected to a range-association memory 209.8 and an association comparator unit 209.9, which is connected by way of its second input to the range-association memory and, on the output side, to the address selector 209.4.

In the comparator unit 209.2 the heart-rate values present at the one input of the unit (and potentially corrected, i.e., periodically affected by fluctuations) are sequentially compared to the pre-programmed limit values of a plurality of heart-rate ranges, the values being stored in the range-limit memory and respectively having specific therapeutic relevance, and the association with one of the ranges is established.

This association is expressed in the type of output signal of the comparator unit 209.2, which is supplied directly to the address selector or pointer 209.3, on the one hand, and, on the other hand, to the association comparator unit 209.9 for comparison of the current value-range association of the measured value with the previous one. The outputs of both comparators 209.2 and 209.9 address the address selector 209.3, which includes, for example, a two-dimensional association table of dosage-value memory addresses for evaluation pairs of the two comparators. Thus, similarly to the situation explained above in reference to FIG. 2, a medication dose to be applied affirmatively is selected from two possible values in overlap zones between two heart-rate ranges as a function of the previous range association of the heart rate (i.e., simultaneously as a function of the previous therapy). As stipulated by this table, the address selector effects the addressing of a specific range of the dosage-value memory 211, that is, the transmission of a specific control variable to the dosing pump.

In the illustrated arrangement, the fluctuation-value processing of the measured variable is likewise effected on the basis of the output signal of the comparator unit 209.2. Depending on the signal characteristic, by passing the filter 209.5 or not, and enabling or blocking the transmission of an actuation signal by the process control 209.1 to the random-number generator 209.7, this signal determines whether the measured heart rate is impressed with a fluctuation value.

The invention is not limited to the preferred embodiments described above. Instead, a plurality of further variations that makes use of the illustrated solution is conceivable.

It is noted that—after the detection of a previously-applied therapy was described above, over the detection of the previous value-range association of the (possibly corrected) measured variable—instead of this, the previous therapy-control variable or even the therapy variable itself can be stored and compared to the therapy-control variable or therapy variable to be applied based on the current range association of the measured variable.

The practical realization of the function blocks of the arrangements shown in the drawings, like the selection of suitable parameters for performing the individual therapies, for example as specific stimulation pulse sequences (or the "VF" therapy as defibrillation shock), lies within the realm of trade by those skilled in the art, and therefore need not be described in detail here. It is pointed out that a realization of the function elements within the scope of a microprocessor control—also with respect to software—is within the spirit of the invention defined in the claims.

We claim:

1. Therapy device, particularly an implantable cardiac pacemaker, cardioverter, combined pacemaker/cardioverter (101) or medication-dosing device (201), having at least one sensor (103; 203) for detecting a variable that can be measured in the application of a predetermined therapy in or on the body of a patient (P) and that particularly characterizes the physical state of the patient, and for outputting a corresponding measured value, the device further having an evaluating and control device (110, 111; 209) that can be at least indirectly connected to the output of the sensor for evaluating the measured value, including its association with one of at least two predetermined value ranges and for determining a therapy control variable as a function thereof, and further having a therapy device (111.3, 111.4, 112; 212), which can be configured for realizing different therapies or therapy variables as a function of the association of the value of the measured variable with one of the value ranges, characterized in that the evaluating and control device includes a range-limit memory (115; 209.3) for storing at least two different limits between two value ranges of the measured variable, and thus at least one overlap zone between the value ranges, a first comparator unit (110.1; 209.2) that is at least indirectly connected to the sensor (103; 203) and, by way of a further input, to the range-limit memory (115; 209.3) for associating the measured value of the variable with one of the value ranges, a therapy memory (111.2; 211) having at least two separately-addressable memory regions for storing at least two different values of the therapy-control variable in association with the values of the measured variable within an overlap zone, together with a predetermined conditional variable that represents the past history of a measured variable or the therapy, and further memory regions for respectively storing a value of the therapy-control variable, in association with a value of the measured variable, outside of an overlap zone, a past-history memory (117; 209.8) for storing the range association of the respectively previous value of the measured variable or of the therapy-control variable of a previously-applied therapy as a conditional variable, and past-history evaluation means (118; 209.9) for evaluating the stored value with the predetermined values of the conditional variable, and for transmitting address data that express the evaluation result to the therapy memory for precisely reading out a value of the therapy-control variable.

2. Therapy device according to claim 1, characterized in that a process control is provided that has a timer (106; 206) such that, with control by the timer, the current value of the measured variable is periodically queried and compared to the stored limits, and an access-control and address signal that effects or prevents a read-out from the therapy memory (111.2, 211) and characterizes the comparison result is outputted.

3. Therapy device according to claim 1, characterized by a configuration of the process control such that an access-control signal is outputted for a read-out from the therapy memory (111.2; 211) after it has been determined that a value-range limit has been exceeded.

4. Therapy device according to claim 1, characterized in that a second comparator unit (118; 209.9) that is connected, on the input side, to the first comparator unit (110.1; 209.2) and the past-history memory (117; 209.8) and, on the output side, to an address selector (116; 209.4) associated with the range-limit memory (115) or therapy memory (111.2; 211) is provided for comparing the current value-range association of the variable with the stored one.

5. Therapy device according to claim 1, characterized by its configuration as an implantable demand pacemaker (111) having a range-limit memory (115), which is configured to store at least one limit between a normal rate range and a bradycardic rate range and two limits and therefore an overlap zone between the normal rate range and a tachycardiac rate range, and a therapy memory (111.2) configured to store at least one bradycardic therapy and one tachycardiac therapy.

6. Therapy device according to claim 5, characterized by the configuration of the range-limit memory (115) to have two memory regions for respectively storing two limits between the normal and the tachycardia rate range and between the tachycardia rate-range and the fibrillation range.

7. Therapy device according to claim 1, characterized by its configuration as an implantable anti-tachycardia/anti-fibrillation device, particularly an anti-tachycardia pacemaker/defibrillator (101), having a range-limit memory (115) that is configured to store at least one limit between a normal rate range and a tachycardia rate range, and at least two limits and thus an overlap zone between the tachycardia rate range and a fibrillation range.

8. Therapy device according to claim 6, characterized in that the range-limit memory (115) has memory regions for two tachycardia rate ranges.

9. Therapy device according to claim 8, wherein said tachycardia rate ranges are adjacent to each other and span an overlap zone which lies between two limits.

10. Therapy device according to claim 1, characterized in that the range-limit memory (115) has two memory regions for storing two limits and thus an overlap zone between the normal and the bradycardia rate range.

11. Therapy device according to claim 1, characterized in that a processing unit (107; 207) connected on the input side to the output of a fluctuation-value generator (108, 108.1; 208, 209.7) is connected between the output of the sensor (103; 203) and the input of the evaluating and control device (110, 111.1, 111.2, 115; 209), with at least one fluctuation value being impressed onto the sensor measured value at at least one time in the processing unit, with control by a time-control unit (106; 206), such that, after the evaluation of the measured value corrected with the fluctuation value or one of the fluctuation values, a value of the therapy control variable that is changed in comparison to the evaluation of the original measured value and/or the measured value corrected with a different fluctuation value is obtained.

12. Therapy device according to one of claim 11, characterized in that the fluctuation-value generator includes a fluctuation-value memory (108) for a plurality of fluctuation values.

13. Therapy device according to claim 12, wherein said fluctuation value generator further comprises a random-number generator (109.1) for respectively selecting one of the stored fluctuation values for impression onto the measure value.

14. Therapy device according to claim 1, characterized in that the sensor (103; 203) is configured to detect an activity variable or a variable that characterizes an organ function of the patient (P).

15. Therapy device according to claim 14, characterized by the configuration of the sensor or the first sensor as an intracardiac electrode (203) having a downstream sensor amplifier (204) for electrical activity of the heart, the device having an associated device for determining the period of electrical cardiac activity as a measured value.

16. Therapy device according to claim 1, characterized in that the sensor (103) is configured to detect the therapy variable.

17. Therapy device according to claim 1, characterized by its configuration as a medication-dosing device (201) such that the sensor or the first sensor (203) is configured to detect the level of an agent, or a variable dependent thereon, in the body of the patient (P) as a measured value, the evaluating and control device (209, 210) is configured to establish a medication dose per time unit, and the therapy device (212) is configured to administer the established dose to the body per time unit.

18. Therapy device according to claim 17, wherein said medication-dosing device (201) is implantable.

* * * * *